(12) United States Patent
Temsamani et al.

(10) Patent No.: US 9,192,654 B2
(45) Date of Patent: Nov. 24, 2015

(54) USE OF THE PAT NANOPEPTIDE IN TREATING AND PREVENTING NEURODEGENERATIVE DISEASES

(75) Inventors: Jamal Temsamani, Nimes (FR); Claude Laruelle, Villeneuve-Loubet (FR)

(73) Assignee: CLL PHARMA, Nice (FR)

( * ) Notice: Subject to any disclaimer, the term of this patent is extended or adjusted under 35 U.S.C. 154(b) by 0 days.

(21) Appl. No.: 13/809,805

(22) PCT Filed: Jul. 11, 2011

(86) PCT No.: PCT/FR2011/000410
§ 371 (c)(1),
(2), (4) Date: Jan. 11, 2013

(87) PCT Pub. No.: WO2012/007658
PCT Pub. Date: Jan. 19, 2012

(65) Prior Publication Data
US 2013/0116193 A1    May 9, 2013

(30) Foreign Application Priority Data

Jul. 12, 2010   (FR) ...................................... 10 02965

(51) Int. Cl.
*A61K 38/32*  (2006.01)
*A61K 38/08*  (2006.01)
*A61K 38/22*  (2006.01)

(52) U.S. Cl.
CPC ................ *A61K 38/32* (2013.01); *A61K 38/08* (2013.01); *A61K 38/22* (2013.01)

(58) Field of Classification Search
None
See application file for complete search history.

(56) References Cited

U.S. PATENT DOCUMENTS

| 5,112,810 | A | 5/1992 | Nagai et al. |
|---|---|---|---|
| 2005/0261194 | A1 | 11/2005 | Dardenne et al. |
| 2006/0159626 | A1* | 7/2006 | Frey, II .......................... 424/45 |
| 2008/0306048 | A1* | 12/2008 | Kaplan et al. ................. 514/218 |
| 2011/0098223 | A1 | 4/2011 | Temsamani et al. |

FOREIGN PATENT DOCUMENTS

| CA | 2026306 | 4/1991 |
|---|---|---|
| EP | 0 425 828 | 5/1991 |
| FR | 2 830 451 | 4/2003 |
| FR | 2 930 156 | 10/2009 |

OTHER PUBLICATIONS

Rafii and Aisen 2009 "Recent developments in Alzheimer's disease therapeutics" BMC medicine 7:7.*
Lennard et al. 2000 "Interleukin-1 beta, interleukin-5, interleukin-6, interleukin-8, and tumor necrosis factor-alpha in chronic sinusitis: response to systemic corticosteroids" Am J Rhinol 14(6):367-73.*
Bachem "Peptide calculator" accessed from www.bachem.com on Dec. 18, 2014.*
Innovagen "Peptide property calculator" accessed from www.innovagen.com on Dec. 18, 2014.*
Wikipedia.org "Route of Administration" accessed from en.wikipedia.org on Dec. 17, 2014.*
Dictionary.com "Perenteral" accessed from dictionary.reference.com on Dec. 17, 2014.*
Reggiani et al. 2006 "Gene therapy for long-term resotration of circulating thymulin in thymectomized mice and rats" Gene therapy 13:1214-1221.*
International Search Report for PCT/FR2011/000410, mailed Jan. 27, 2012, (Fayos, Cecile).
Safieh-Garabedian B. et al., "Thymulin reverses inflammatory hyperalgesia and modulates the increased concentration of proinflammatory cytokines induced by i.c.v. endotoxin injection", Neuroscience, vol. 121, No. 4, (2003), pp. 865-873.
Morel, G.R. et al., "Peripheral and mesencephalic transfer of a synthetic gene for the thymic peptide thymulin", Brain Research Bulletin, vol. 69, No. 6, (May 31, 2006), pp. 647-651.
Haddad, J.J. et al., "Thymulin: An emerging anti-inflammatory molecule", Current Medicinal Chemistry—Anti-Inflammatory & Anti-Allergy Agents, vol. 4, No. 3, (Jun. 2005), pp. 333-338.
Licastro, F. et al., "Zinc and thymic hormone-dependent immunity in normal ageing and in patients with senile dementia of the Alzheimer type", Journal of Neuroimmunology, vol. 27, No. 2-3, (May 1, 1990), pp. 201-208.
Davis, L.J. et al., "Plasmatic activity of thymulin : Comparison of free and protein bound thymulin in Alzheimer's disease", Advances in the Biosciences ; Alzheimer's Disease and Related Disorders, (Jul. 12-17, 1993), pp. 279-280.
Hansch et al, "Exploring QSAR Fundamentals and Applications in Chemistry and Biology", ACS Professional Reference Book, American Chemistry Society, Washington, DC 1995, pp. 388-409.
Pajouhesh et al, "Medicinal Chemical Properties of Successful Central Nervous System Drugs", The Journal of the American Society for Experimental NeuroTherapeutics, vol. 2, No. 4, Oct. 2005, pp. 541-553.
Reichel, "The Role of Blood-Brain Barrier Studies in the Pharmaceutical Industry", Current Drug Metabolism, 2006, 7 183-203.

\* cited by examiner

*Primary Examiner* — Gregory S Emch
*Assistant Examiner* — Adam M Weidner
(74) *Attorney, Agent, or Firm* — Young & Thompson

(57) ABSTRACT

The invention relates to the use of the PAT nonapeptide in the manufacture of a drug for preventing or treating a neurodegenerative disease such as Alzheimer's disease. The parenteral route of administration is preferable, including the subcutaneous, intraperitoneal, intravenous or intranasal routes. The invention also relates to an injectable formulation containing the PAT nonapeptide which can be administered to patients suffering from a neurodegenerative disease such as Alzheimer's disease.

5 Claims, 4 Drawing Sheets

Figure 1: Measurement of spontaneous alternation during the Y maze test. The PAT peptide is injected by intra-cerebroventricular (i.c.v) route.
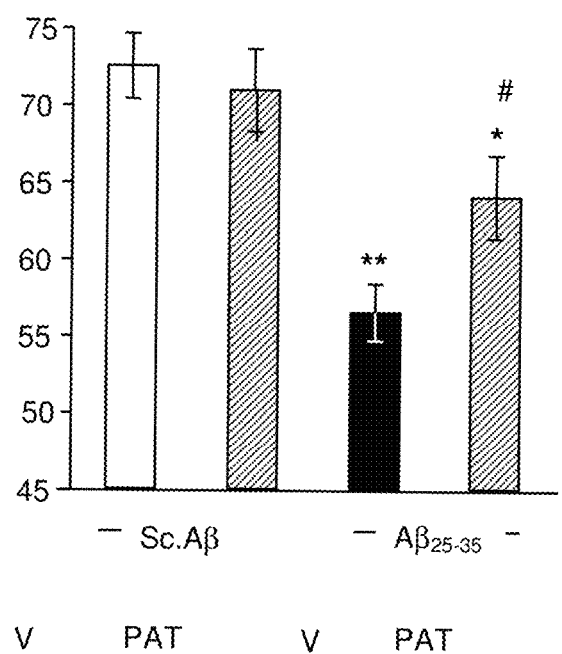

Figure 2A: Passive avoidance test: measurement of latency time to enter in the dark compartment. Injection of the PAT peptide (5µg) by i.c.v route.
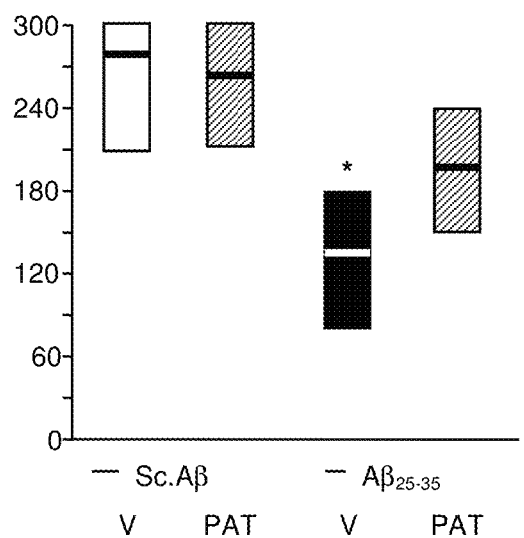
Figure 2B: Passive avoidance test: measurement of latency time for the escape. Injection of the PAT peptide (5µg) by i.c.v route.
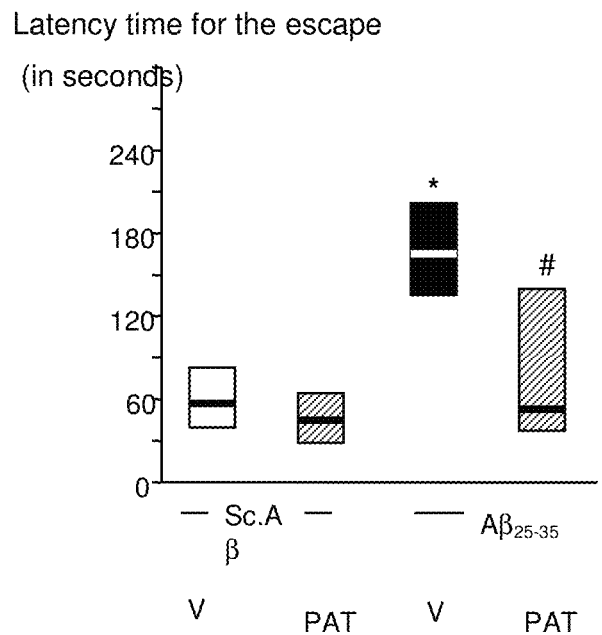

Figure 3 : Y-maze test : measurement of spontaneous alternation. Injection of the PAT peptide by intra-peritoneal (i.p.) route.
Spontaneous alternation (%)
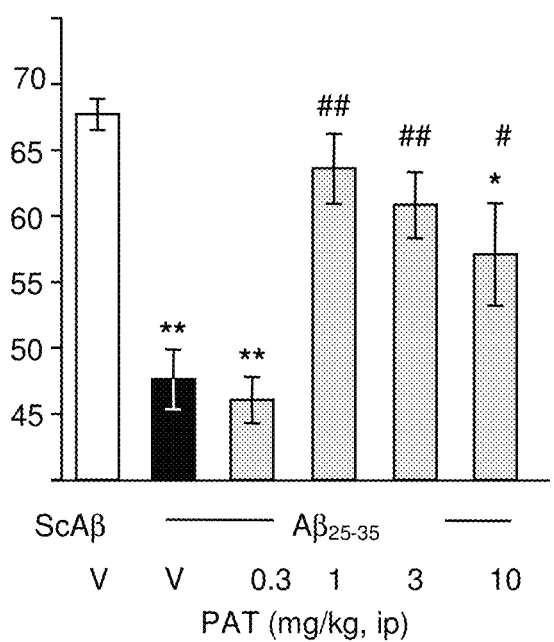

Figure 4A. Passive avoidance test : measurement of latency time to enter in the dark compartment. Injection of the PAT peptide using i.p route.
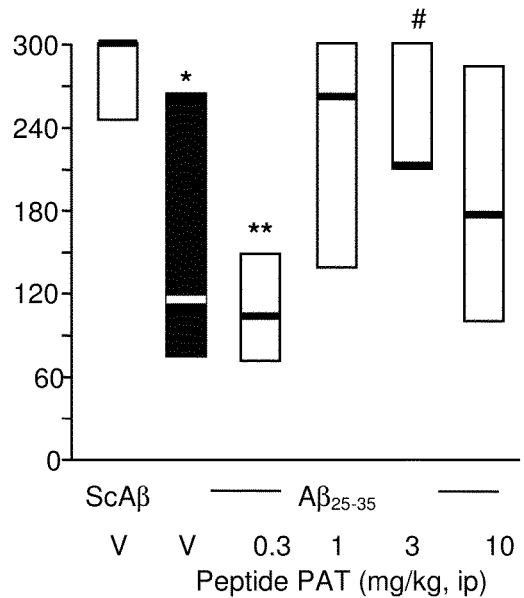
Figure 4B. Passive avoidance test : measurement of latency time for escape. Injection of the PAT peptide by i.p route.
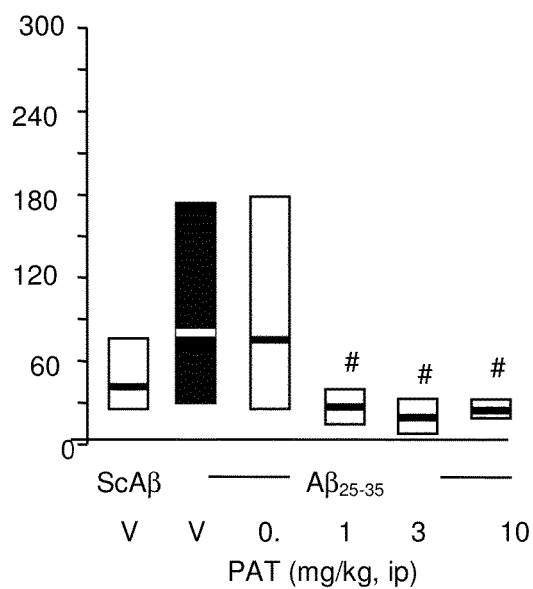

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Peptide Analog of Thymulin nonapeptide

<400> SEQUENCE: 1

Glu Ala Lys Ser Gln Gly Gly Ser Asp
1               5
```

USE OF THE PAT NANOPEPTIDE IN TREATING AND PREVENTING NEURODEGENERATIVE DISEASES

This application is the U.S. national phase of International Application No. PCT/FR2011/000410, filed 11 Jul. 2011, which designated the U.S. and claims priority to France Application No. 10/02965, filed 12 Jul. 2010, the entire contents of each of which are hereby incorporated by reference.

The invention concerns the use of the PAT nonapeptide for the manufacturing of a drug in the treatment or the prevention of neurodegenerative diseases such as Alzheimer's disease.

The neurodegenerative diseases affect progressively the brain function and more generally the nervous system. The process involved consists generally in a deterioration of the functioning of the nervous cells, in particular the neurons, leading to the cellular death. The consequence for the patient is a progressive alteration, usually irreversible, of the nervous functions which can induce his death. The clinical outcome can be either some damages of the psychic function, leading to dementia such as in Alzheimer's or Pick's disease, or motor abnormalities such as in amyotrophic lateral sclerosis or Parkinson's disease, or the combination of both such in Huntington's chorea disease or Creutzfeidt-Jacob's disease.

Alzheimer's disease (AD) is the most known and spread of the neurodegenerative diseases. It is characterized by memory loss and sometimes by disorders of reasoning, organization, language and perception. It is widely admitted that the AD symptoms arise from an increase of the production or accumulation of a specific protein (β-amyloid) in the brain, which leads to the death of nervous cell. Increasing age is the greatest know risk factor for AD. Approximately 30 millions of people in the world are affected by AD. Population ageing suggests that the economic burden caused by AD disease will become increasingly important.

Albeit, there is currently no treatment leading to the AD recovery, there are 2 types of drugs which can decrease its symptoms and slow down its evolution. EP 236684A, DE 3305744A and EP 296560A disclose drugs based on acetyl-cholinesterase inhibitors: galantamin, rivastigmin and donepezil respectively. EP392059A discloses a drug containing memantin which is a NMDA receptor antagonist. All these drugs have received a marketing authorization to treat AD. However, the treatment only affects the symptoms. Several studies have shown that these drugs slow down only in a modest way the progression of cognitive symptoms as well as erratic behaviors in some patients. Moreover, half of the patients who received these drugs do not respond to these treatments. Finally, these drugs induce several undesirable effects such as nausea, diarrhea, hepatic disorders etc. . . . . Thus, there is an urgent need for drugs with a new mechanism of action different from the aforementioned drugs. Several projects are being explored currently. Few examples are mentioned hereafter.

The secretase inhibitors block the transformation process of the β-amyloid protein precursor (known as "APP") into the β-amyloid protein and thus permit to slow down its dangerous accumulation in the brain. Among these Inhibitors is the tramiprosate (Alzhemed®) which was tested in a phase II clinical study (Aisen P S, Salmon gaff D, Briand R and al., Neurology, Nov. 2006 28; 67(10): 1757-63). Another inhibitor, the scillo-cyclohexanehexol was tested in animals successfully (Mac Larin J A et al.; Nature Medicine 12.801-808 (2006). These molecules interact with β-amyloid proteins during their formation and prevent them from agglomerating and from forming small aggregates, which destroy nervous cells by settling as solid plaques. However, they already cause important damage during their formation.

Other treatments such as ubiquitin (compound naturally produced in the brain) induce the disappearance of β-amyloid protein before its reaches high accumulation in the brain (Taddei et al.; Neuroscience letters; 1993, vol. 151, no 2, pp. 158-161). However, the ubiquitin rates remain insufficient in patients which suffer from Alzheimer's disease.

Another interesting method is the immunological approach. WO 94/06476A discloses a new type of drug which has a target different from the molecules cited previously: Etanercept (ENBREL®), which is a fusion protein directed against the TNF-α (tumor necrosis Factor) pro-inflammatory cytokine. A recent pilot study was carried out over a 6 months period and showed encouraging results in term of cognitive improvement (Tobinick E; CNS Drugs; 2009; 23; 713-25). In addition to the fact that the project is at a preliminary phase at the clinical level, the administration of the product ENBREL® was carried out by perispinal route in order to circumvent the problem linked to its incapacity to pass across the blood-brain barrier (BBB) (Griffin S; Newspaper of Neuroinflammation; 2008; 5: 3). However, this route of administration is burdensome and painful for the patient and requires a certain number of precautions: It must be carried out in hospitals. The presence of the blood-brain barrier (BBB) restricts strongly the passage of molecules such as ENBREL from the plasma into the cerebral extracellular medium: very few drugs designed in laboratories, cross this barrier to treat brain diseases.

Therefore, there is a need for drugs which should at the one hand be sufficiently effective to treat AD, and on the other hand cross the BBB. The Applicant objective is to develop a drug capable to treat of Alzheimer's disease without presenting the disadvantages of the existing treatments. The Applicant has found, in a fortuitous way, due to the work already carried out with this molecule, that a peptide analog of thymulin hormone has an interesting potential in the prevention and the treatment of AD.

We know since the late 1950's the central role played by the *thymus* in the differentiation of T-cells, responsible in particular of transplant rejection and implicated in the immune defense against the viruses and some bacteria. The hormone secreted by the *thymus* was then identified as a peptide of 9 amino-acids: the thymulin (Bach et al. Pleau et al. Immunol letters, 1979; 1:179-182; Amor and al., Annals of the Rheumatic Diseas 1987: 46: 549-554). The thymulin effects on the immune system were shown to be zinc-dependent. Indeed, zinc confers to the thymulin a tetrahedral conformation which corresponds to the active form of the molecule. In the absence of zinc, thymulin is no longer active on the immune system. Work was undertaken specifically on a nonapeptide called "PAT" having the sequence of amino-acids Glu-Ala-Lys-Ser-Gln-Gly-Gly-Ser-Asp (EAKSQGGSD (SEQ ID NO:1)). The application WO 03/030927A reports that several derivatives of thymulin, such as the PAT nonapeptide presents analgesic and anti-inflammatory properties, and can treat in pain including neurogenic pain. More recently, the application WO 2009/150310A describes specifically the use of the PAT nonapeptide in the treatment of autoimmune diseases such as rheumatoid arthritis, and intestinal bowel diseases (IBD) such as Crohn's disease and hemorrhagic rectocolitis.

The present invention refers to the use of the PAT nonapeptide of sequence (SEQ ID NO:1) responding to the formula (I):

EAKSQGGSD;

or one of its pharmaceutically acceptable salts in the preparation of a drug in the treatment and the prevention of neurodegenerative diseases, in particular Alzheimer's disease.

The PAT peptide is administered to the human or the animal at a dose ranging between 0.1 and 50 mg; and preferably between 1 and 10 mg. By "pharmaceutically acceptable salt", one understands as example and in a nonrestrictive way acetate, sulphate or hydrochlorate. The invention also relates to the use of a compound of formula (I) in which one or more amino-acids are in the D configuration.

The pharmaceutical composition of the invention can be administered by parenteral, topical oral perlingual, rectal or intraocular route. The preferred administration route is the parenteral route, and in particular the cutaneous (s.c.), intranasal, intra-peritoneal (i.p.) or intravenous (i.v) routes. It can also be considered a topical route, in particular transdermal, such as for example, as a patch, pomade or gel.

During an experiment carried out for the invention, it was shown that the PAT nonapeptide displays a biological activity when it is administered by intracerebroventricular (i.c.v) route—which bypasses the BBB—, and also by parenteral route (intra-peritoneal). This latter mode of administration highlights the fact that that the product crosses the BBB and reaches the brain. To cross the BBB, persons skilled in the art know that the molecular and physicochemical properties of the molecule must fulfill the 5 criteria described by Lipinski and al. (1997). Adv Drug Del Rev 23: 3-25 (amongst them a low molecular weight, its lipophilicity, its charge etc. . . . ). Yet, we were surprised to notice that the PAT peptide, which does not fulfill all these criteria, crosses the BBB.

The formulations to be administered by parenteral route contain a solvent allowing the solubilization of a peptide such as the PAT peptide; this solvent can be selected among the water for injection or physiological saline solution, optionally with preservative agents (such as cresol, phenol, benzyl alcohol or methylparaben) and/or buffer agents, and/or isotonic adjuvants and/or surfactants well-known by persons skilled in the art.

One of the preferred administrations is the subcutaneous (s.c.) route. The injectable form by subcutaneous route according to the invention contains the PAT peptide dissolved in an appropriate solvent, with if necessary other excipients such as those cited previously. One of the injectable subcutaneous forms according to the invention contains a polymer which allows a slow diffusion of the PAT peptide during the time course (period up to 30-40 days). In order to achieve that, PAT peptide is dissolved in an appropriate solvent such as a physiological saline solution, and mix with appropriate polymers such as the polyethylene glycols, polyvinyl pyrrolidones and polyacrylamides.

Other advantages and characteristics of the invention will become clear upon reading the following examples. Reference is made to the appendix drawings in which:

FIG. 1 shows the results obtained from Y-maze test in mice having received by (i.c.v) intracerebroventricular route either the ScAβ ("scrambled") peptide or the Aβ$_{25-35}$ peptide, and also by intra-cerebroventricular (i.c.v) route an inert (V) vehicle or the PAT peptide. The evaluated parameter is the spontaneous alternation expressed as a percentage;

FIG. 2 shows the results obtained from passive avoidance test; the treated groups are identical to those of FIG. 1; in FIG. 2A is measured the latency time (in seconds) to enter into the dark compartment; and in FIG. 2B is measured the latency time to escape (in seconds);

FIG. 3 shows the results obtained from Y-maze test under the same conditions as for FIG. 1, except that the PAT peptide and the inert (V) vehicle are injected by intra-peritoneal (i.p.) route;

FIG. 4 shows the results obtained from passive avoidance test carried out such as for FIG. 2 except that the PAT peptide and the inert (Y) vehicle are injected by intra-peritoneal (i.p.) route; in FIG. 4A is measured the latency time (in seconds) to enter into the dark compartment; and in FIG. 4B is measured the latency time to escape (in seconds).

In the figures presented above, Dunnett's test was applied to the results: (*) means that the results are significant with a probability of <0.0001; (**) with a $p<0.01$ vs. ScAβ+V treatment group; (#) with a $p<0.05$ vs. (Aβ25-35+V) treatment group and (##) with a $p<0.01$ vs. (Aβ25-35+V) treatment group.

EXAMPLE 1

Alzheimer'S Model in Mice—Spontaneous Alternation Test

Experimental Protocol

The Swiss OF-1 (Depré, St Doulchard, France) mice are 7-9 weeks old from and weigh 32±2 g. They are dispatched into several groups and placed in plastic cages. They have free access to food and water, except during the behavioral experiments, and are maintained in an environment controlled (23±1° C., 40-60% of moisture) with light/darkness cycles of 12 hrs (light on at 8:00 am). The experiments are carried out between 9:00 am and 5:00 pm, in a room of experimentation. The mice are acclimated during 30 minutes before the beginning of the experiment. All the protocols followed the directives of the European Union dating of Nov. 24, 1986.

Treatment

The PAT peptide (5 μg) synthesized by Polypeptide (Denmark) is solubilized in distilled water and was administered by infra-peritoneal (i.p.) route in a volume of 100 μl (by 20 g of body weight) or by intra-cerebroventricular (i.c.v.) route at the same time as the amyloid peptide. The β[25-35] amyloid peptide called Aβ$_{25-35}$ and the Aβ25-35 "scrambled" peptide—called Sc.Aβ—were purchased from Genepep (France). They are resuspended in sterile distilled water at a concentration of 3 mg/ml and are preserved at 20° C. until their use. Before being injected, the peptides are subjected to an aggregation at 37° C. during 4 days. They are administered by i.c.v route in a final volume of 3 μl per mouse. The animals are tested at Day 7 after the injection.

In a first set of experiments, the mice received intracerebral (i.c.v.) administration of either water, or PAT nonapeptide (5 μg) at the same time than the ScAβ peptide or the Aβ$_{25-35}$ peptide (9 nmol). After a 7-days period, their performance in the spontaneous alternation test was evaluated. The numbers of animals per group were respectively 10 and 11. In a $2^{nd}$ set of experiments, the same test was performed, except that the PAT peptide Is administered by intra-peritoneal (i.p.) route.

Test Course—Measured Parameters

We place each mouse, which is not familiar with the device, at an end of a Y-maze (3 arms of 50 cm length and separated from 60°) and we let it move freely during 8 minutes. The number of entries in each arm, including the possible returns in the same arm, is counted visually. An entry is counted when the forelegs of the animal come at least 2 cm in the arm. An alternation is counted when an entry is made in all the 3 arms during successive tests. The number of total possible alternations is then the total number of entries minus 2 and the percentage of alternations is calculated as: (counted alternations/total of possible alternations)×100. The animals making less than 8 entries in 8 minutes are discarded from the experimental groups. No animal was excluded in this study. The compounds are administered 30 minutes before the session.

Results

The results are shown in FIG. 1 and FIG. 3 for the i.c.v and i.p administration routes, respectively.

As expected, when the $A\beta_{25-35}$ peptide is administered, the symptoms of Alzheimer's disease are induced. Administration of the control ScAβ peptide had no effect.

As expected, we observe that in FIG. 1 (i.c.v.) route when the Sc.Aβ peptide is administered to the mice (which do not show any symptom of Alzheimer's disease); the co-administration of the PAT peptide has no effect. In contrast; co-administration of PAT peptide with the $A\beta_{25-35}$ peptide (thus the mice reproduce memory symptoms), exerts a significant neuroprotector effect on learning deficits induced by the $A\beta_{25-35}$ peptide.

In FIG. 3 (i.p. route), we also notice a neuroprotector effect of the PAT peptide and that this effect is very significant for the dose of PAT peptide between 1 and 3 mg/kg of body weight.

EXAMPLE 2

Alzheimer'S Model in Mice—Passive Avoidance Test

Experimental Protocol

The Information relative to the mice, the peptides, their administration and the treatment groups are similar to those of Example 1.

Test Course. Tested Parameters

The compounds are administered 30 minutes before the test. This test allows the evaluation of the long term non-spatial memory. The device in the test consists of an enlightened compartment having white PVC walls (with width/length/height dimensions of 15-20-15 cm respectively); an obscure compartment having black PVC walls (with same dimensions) and a grid on the ground. A trap door separates the 2 compartments. A lamp of 60 W is positioned 40 cm above and lightens the white compartment during the experiment. On the grid, random electric shocks of 0.3 mA are delivered to the mice legs during 3 seconds from a random power generator (Lafayette Instruments, USA).

The $1^{st}$ phase of the experiment called "training" is carried out first. The trap door is closed at the beginning of the exercise. Each mouse is placed in the white compartment. The trap door is lifted after 5 seconds. When the mouse enters into the dark compartment and touches the grid with all its legs, the trap door is closed and the random electric shock is delivered on the legs during 3 seconds. The latency time before the entry into the dark compartment and the number of counts are recorded. The number of counts do not differ between the groups, indicating that the sensitivity to the electric shock is not affected by the type of administration route i.e. here i.c.v or i.p (not shown results). The animals for which the latency time is out the range of 3-30 seconds are discarded from the experiment. The attrition rates for less than 2% of the animals and is independent of the treatment.

The $2^{nd}$ phase of the experiment called "retention" is carried out 24 h after the $1^{st}$ phase ("training"). Each mouse is placed again in the white compartment. The trap door is raised after 5 seconds. The latency time of entry into the dark compartment is recorded during a 300 seconds period. The number of entries and the time of escape (time spent going back into the white compartment) are measured during a 300 seconds period.

Results

The results are presented in FIG. 2 (2A and 2B) for the administration by i.c.v route; and in FIG. 4 (4A and 4B) for the administration by i.p route.

The FIG. 2—administration by i.c.v route—shows clearly that the injection of the PAT peptide (5 μg) by i.c.v route in mice having received the $A\beta_{25-35}$ peptide (the latter reproducing training deficits) improves the 2 criteria tested when they are compared to mice having received water distilled (V) only. Thus, by using this animal model of Alzheimer's disease, it is demonstrated that the PAT peptide presents at a significant neuroprotector effect.

Again, in FIG. 4—administration by i.p. route—a neuroprotector effect of PAT peptide is observed. As in the spontaneous alternation test, the neuroprotector effect of the PAT is observable for a dose higher than 0.3 mg/kg of body weight.

Thus, the use of the 2 animal models of Alzheimer's disease shows that the PAT peptide is an interesting and promising candidate to treat and prevent cerebral lesions related to the training deficit.

The invention claimed is:

1. A method of treating Alzheimer's disease comprising administering, by parenteral route, an effective amount of the PAT nonapeptide of formula (I): EAKSQGGSD (SEQ ID NO: 1), or a pharmaceutically acceptable salt thereof, in a pharmaceutical composition to a person in need of such treatment,
wherein said administered PAT nonapeptide or pharmaceutically acceptable salt crosses the blood-brain barrier and reaches the brain.

2. The method of claim 1, wherein said administering comprises subcutaneous, intra-peritoneal, intravenous or intranasal administration.

3. The method of claim 1, wherein the effective amount of said PAT nonapeptide is administered in a dose ranging between 0.1 mg and 50 mg.

4. The method of claim 3, wherein the dose is in a range of between 1 mg and 10 mg.

5. The method of claim 1, wherein at least one amino acid of the PAT nonapeptide is in the D configuration.

* * * * *